United States Patent
Brosmith

(10) Patent No.: US 9,022,365 B2
(45) Date of Patent: May 5, 2015

(54) SCENT DIFFUSER

(71) Applicant: Maesa, Inc., New York, NY (US)

(72) Inventor: Sean Brosmith, Los Angeles, CA (US)

(73) Assignee: Maesa, Inc., New York, NY (US)

( * ) Notice: Subject to any disclaimer, the term of this patent is extended or adjusted under 35 U.S.C. 154(b) by 207 days.

(21) Appl. No.: 13/891,600

(22) Filed: May 10, 2013

(65) Prior Publication Data

US 2014/0332990 A1    Nov. 13, 2014

(51) Int. Cl.
*B01F 3/04* (2006.01)
*A61L 9/12* (2006.01)

(52) U.S. Cl.
CPC .............. *A61L 9/127* (2013.01); *B01F 3/04085* (2013.01)

(58) Field of Classification Search
CPC ................................ B01F 3/04; B01F 3/04085
USPC ......... 261/26, 30, 94, 142, DIG. 88, DIG. 89; 239/53, 55, 56, 57
See application file for complete search history.

(56) References Cited

U.S. PATENT DOCUMENTS 5,851,442 A * 12/1998 Spector ........................... 261/30
2013/0049236 A1 * 2/2013 Garon et al. ..................... 261/26

* cited by examiner

*Primary Examiner* — Robert A Hopkins
(74) *Attorney, Agent, or Firm* — Sandy Lipkin

(57) ABSTRACT

A scent diffuser method and apparatus that uses a sealed dry technology scent either alone in as part of a cartridge that is inserted into a housing and wherein the sealed scent cartridge is actuated to expose it to the immediate environment thereby allowing the scent to be diffused throughout the immediate proximity. The scent is activate through the use of a fan or the application of heat through a power source. As a stand alone unit, a device using the cartridge is activatable through the depression of a knob that is powered by a spring to keep it open and closed as desired. Once open, the knob can be rotated to control the speed of scent diffusion.

2 Claims, 8 Drawing Sheets

SCENT DIFFUSER

BACKGROUND OF THE INVENTION

1. Field of the Invention

The present invention, relates generally to the field of scent diffusers, and more specifically toward a new method of diffusing scent that uses dry technology cartridges that are housed inside the diffuser and the scent diffused through the immediate proximity through an actuator that can be a fan that is electrically powered or through the direct application of heat or both.

2. Description of the Prior Art

Scent diffusers are used to provide environmental ambience through the use of scents. This can be accomplished with scented candies, incense and oil burners. Other prior art systems for scent diffusion typically involve a glass vessel filed with liquid fragranced oil that is diffused by heating a ceramic wick through an electric current.

SUMMARY OF THE INVENTION

The preferred embodiment of the present invention teaches a scent diffusing device comprising: a porous substrate infused with concentrated fragrance oil wherein said concentrated fragrance oil can be passively dispersed through the immediate environment or actively dispersed through the actuation of a mechanism to excite the scent molecules in said concentrated fragrance oil.

The above embodiment can be further modified by defining that said diffusing device is housed in a cartridge, said cartridge further comprising: an outer casing; an interior portion defined by said outer casing wherein said diffusing device can be housed; a cover on said outer casing with a plurality of apertures to allow the diffusion of scent from said paid therethrough through upon actuation of said mechanism.

The above embodiment can be further modified by defining that said actuation is achieved through a fan.

The above embodiment can be further modified by defining that said fan is powered through an electricity source.

The above embodiment can be further modified by defining that said actuation is achieved through the application of heat.

The above embodiment can be further modified by defining that said application of heat is achieved through the plugging into an electrical socket.

The above embodiment can be further modified by defining that said scent diffuser is inserted into a stand alone unit, said stand alone unit further comprising: a base portion; an electrically powered fan secured in said base portion; an outer housing situated atop said base portion; an inner chamber formed inside of said outer housing and atop said base portion; a scent cartridge housing for said scent cartridge situated inside said inner housing; an actuator to allow for the release of scent from said scent diffuser.

The above embodiment can be further modified by defining that said actuator is located on said top portion and is released through a spring.

The above embodiment can be further modified by defining that said actuator can be radially rotated to allow for control of the speed of release of said scent from said diffuser.

The above embodiment can be further modified by defining that said scent is diffused into the immediate environment through the powering of said electrically powered fan.

The above embodiment can be further modified by defining that said electrically powered fan is powered through an electrical system that uses a power cord that is plugged into a power outlet.

The above embodiment can be further modified by defining that said electrically powered fan is powered through batteries.

DETAILED DESCRIPTION OF A PREFERRED EMBODIMENT

Figure 1:
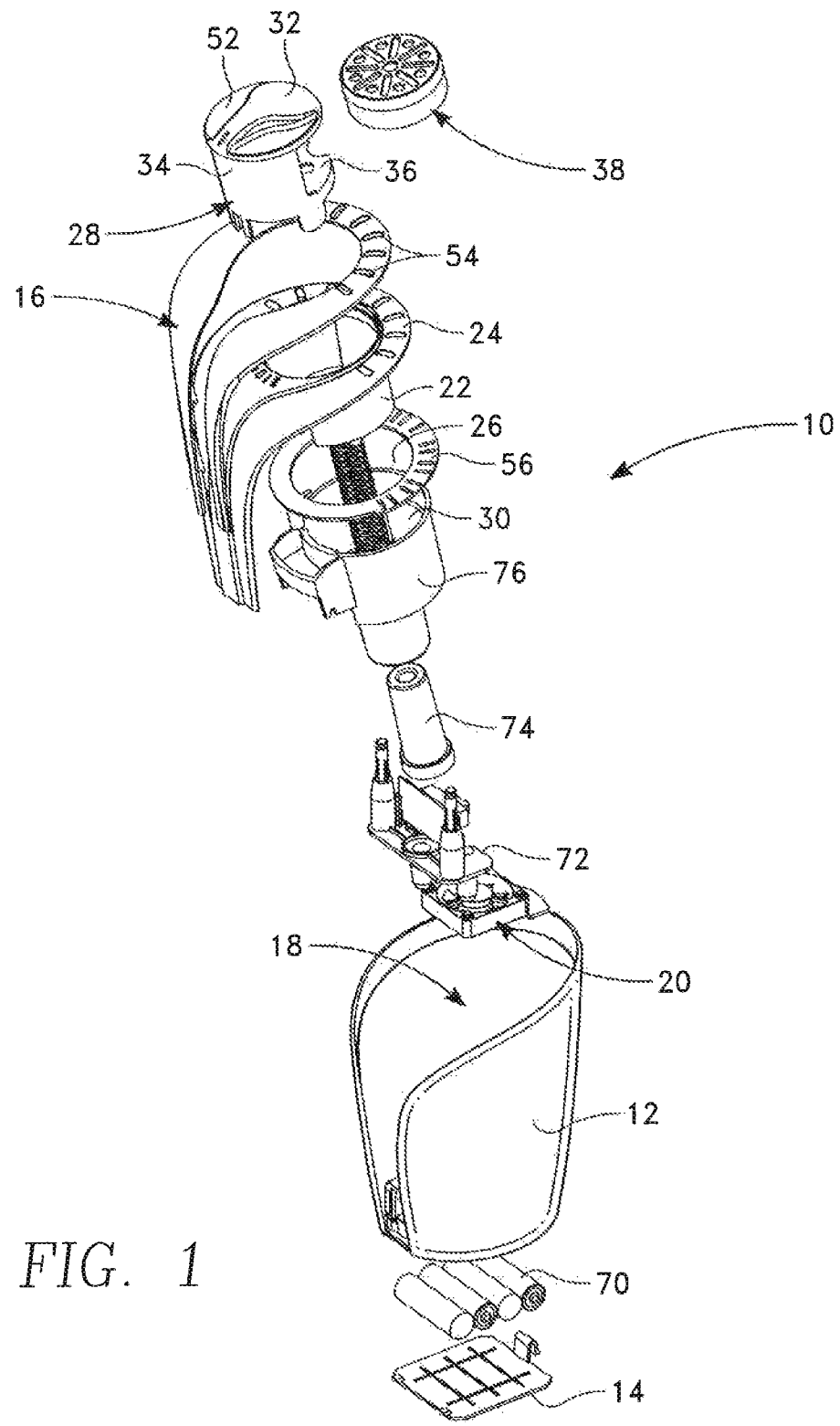
FIG. 1 is an exploded perspective view of the stand alone scent diffuser of the instant invention.
Figure 2:
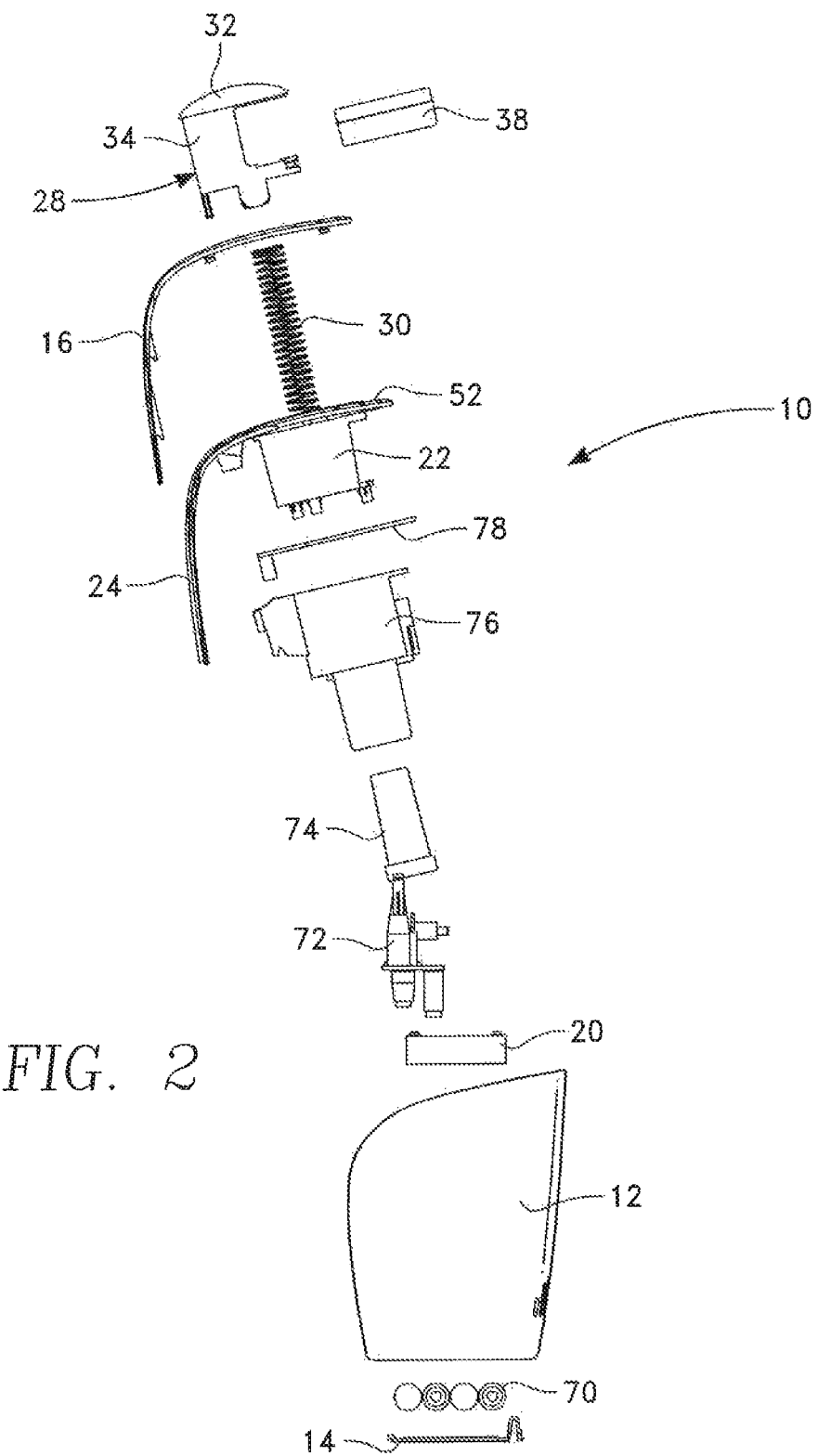
FIG. 2 is a side exploded view of the stand alone scent diffuser of the instant invention.

Turning to the drawings, the preferred embodiment is illustrated and described by reference characters that denote similar elements throughout the several views of the instant invention.

Figure 3:
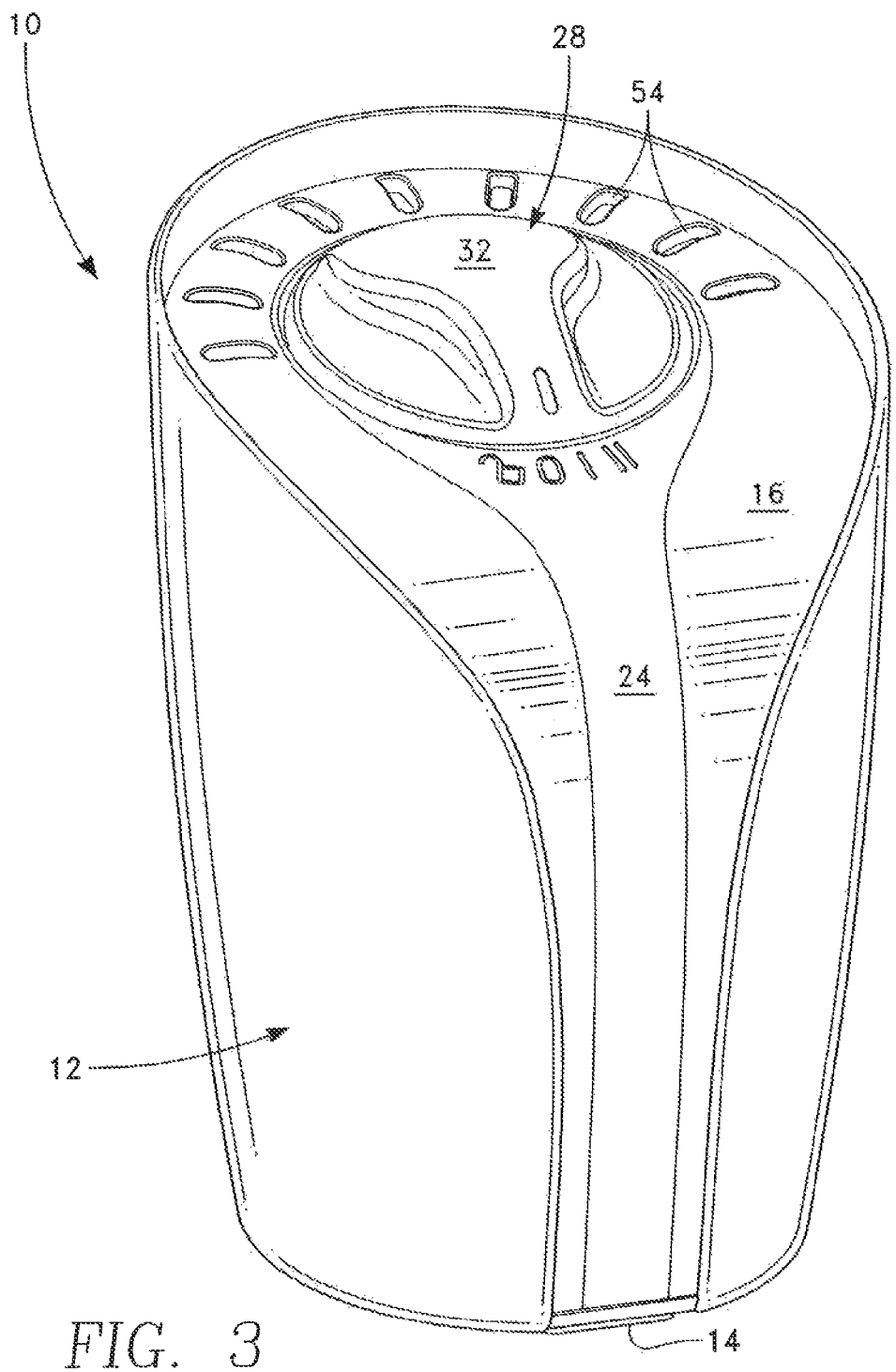
FIG. 3 is a front perspective view of the stand alone scent diffuser of the instant invention in the closed position.
Figure 4:
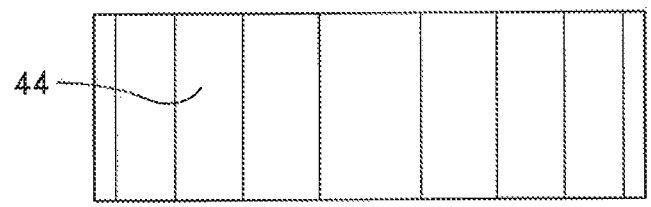
FIG. 4 is a side view of the scent cartridge of the instant invention.
Figure 5:
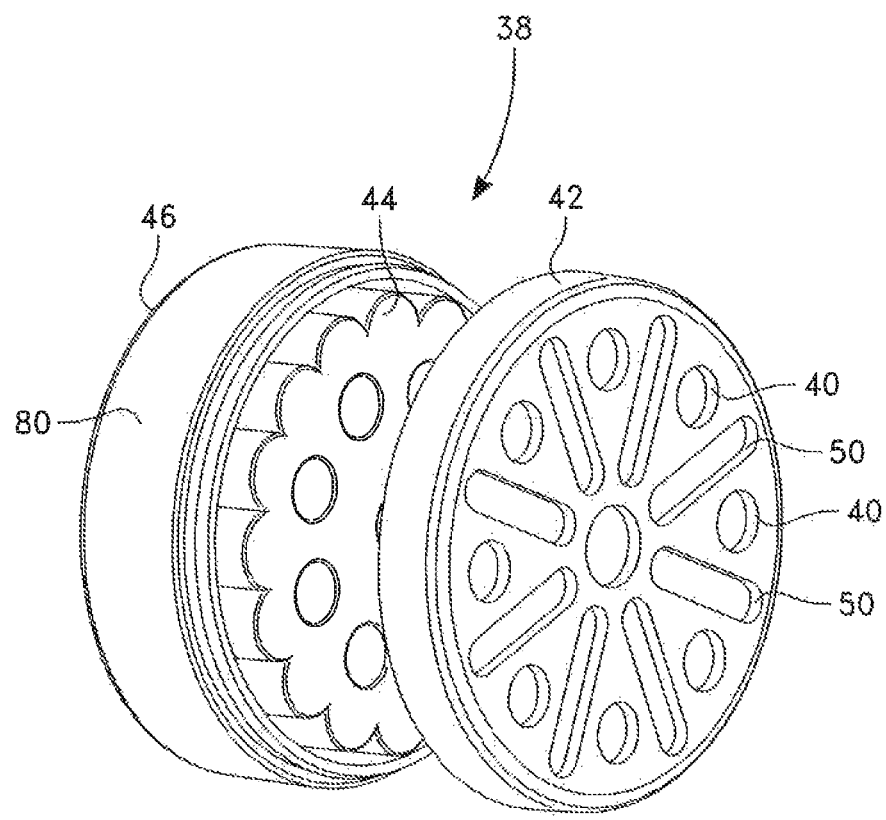
FIG. 5 is an exploded side perspective view of the cartridge of scent diffuser of the instant invention.
Figure 6:
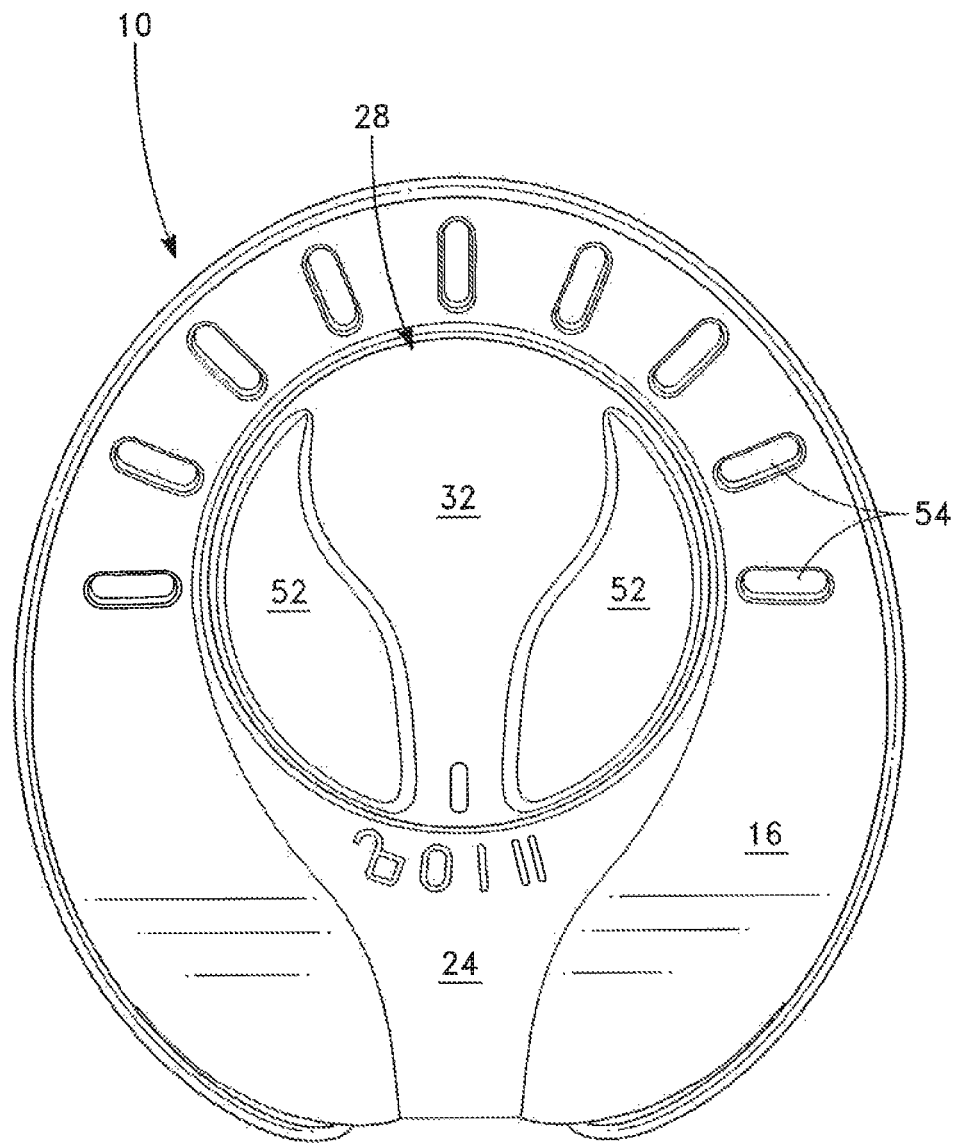
FIG. 6 is a top view of the actuator of one embodiment of the stand alone unit of the instant invention.
Figure 8:
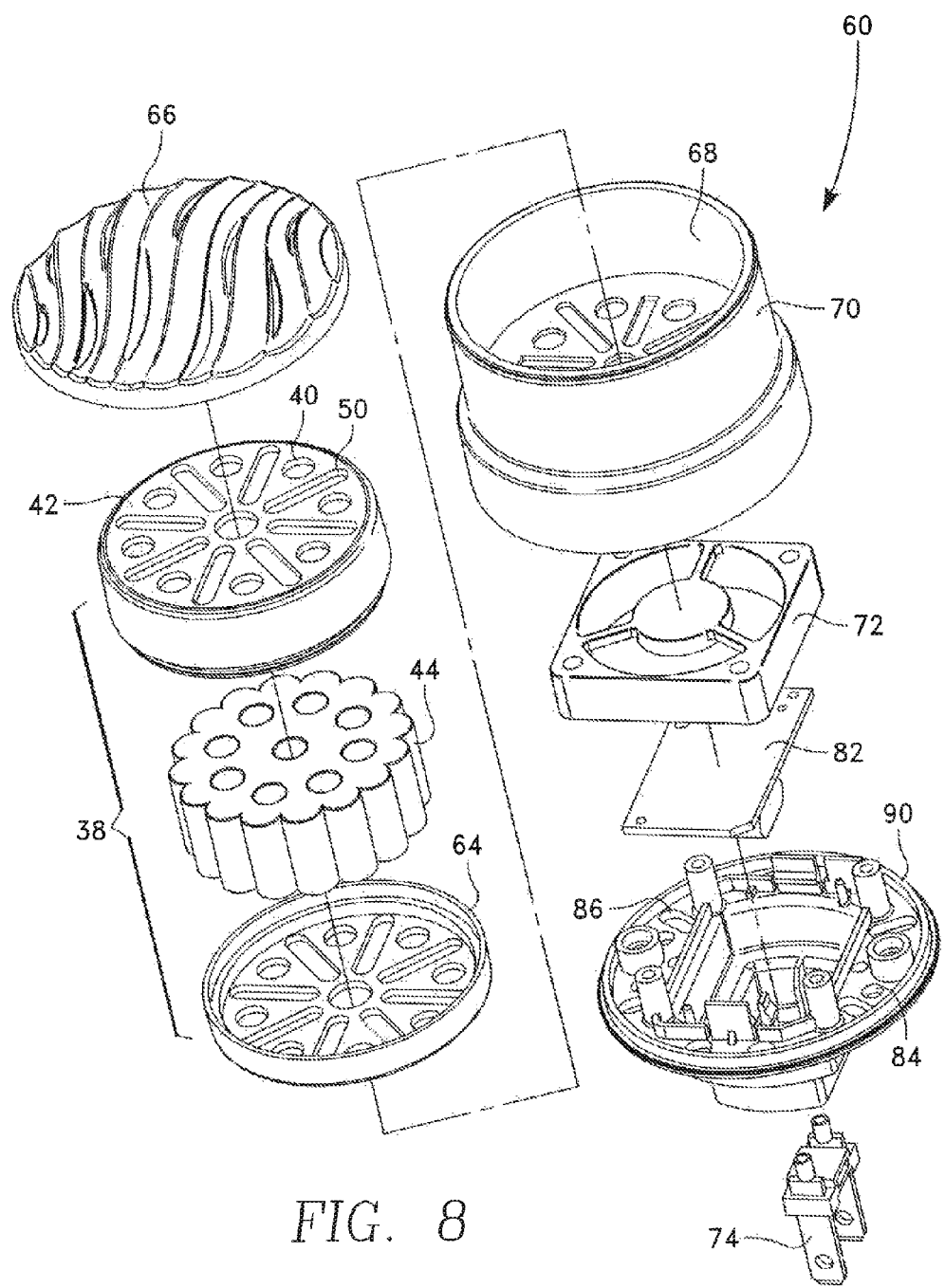
FIG. 8 is an exploded view of a first embodiment of the plug-in unit of the scent diffuser of the instant invention wherein a fan is utilized.
Figure 9:
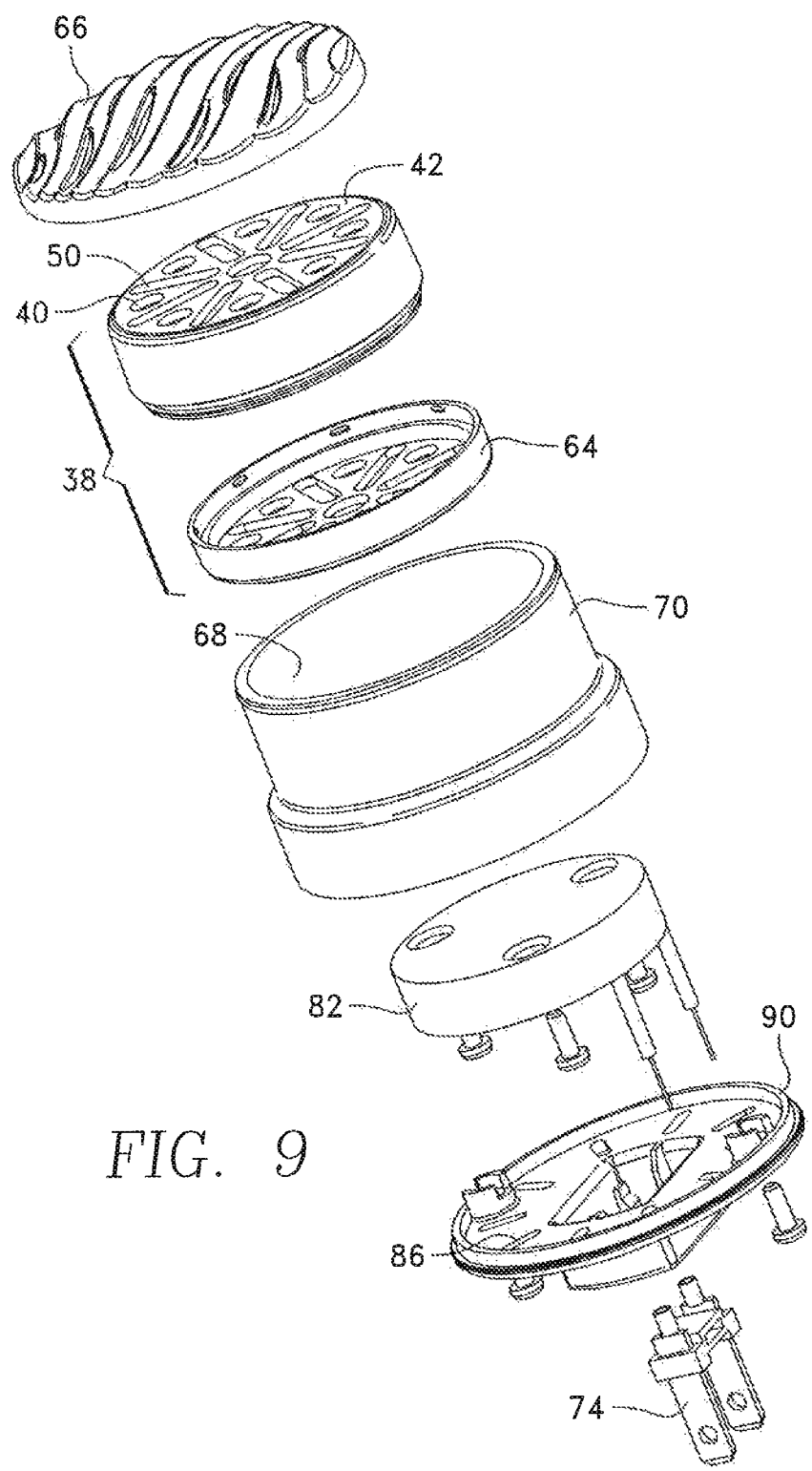
FIG. 9 is an exploded view of a second embodiment of the plug-in unit of the scent diffuser of the instant invention wherein no fan is utilized.

The core of the preferred embodiment of the instant invention is illustrated in detail in FIGS. 4-5 wherein the dry porous substrate infused with fragrance oil is housed in a cartridge. The porous pad can be used in a stand alone unit (FIGS. 1-3, 6-7) or as a plug-in unit (FIGS. 8-9).

The stand alone scent diffuser 10 operates as a single unit that exists in an open position when the scent is a diffusing and a closed position when not in use. The unit 10 is comprised of an outer housing 12 that optionally houses a battery door 14 at the bottom that opens to a cavity that allows for the placement therein of batteries 70. Alternatively, the device could be powered by an electrical cord (not shown) that would be placed in roughly the same position that would allow the entire unit to be plugged into a wall socket.

A decorative top/front panel 16 covers the outer housing 12 and allows the unit to be closed and self-contained when not in use that also includes vents 54 and apertures to allow scent to escape when in use. Between the top panel 16 and the outer housing 12 is an interior space 18 created that allows for the placement therein of the scent diffusing mechanism. Into this interior space 18 can also be placed a fan 20 that is powered by the electrical source that actuates the scent diffusion.

Above the fan 20 is placed mechanical portions 72 that suspend a vertical piece 74 that fits into the center of a housing 76 into which a spring 30 descends from the top and rests therein. Above this housing 76 sits a disc 78 that separates the housing 76 from another rotatable housing 22 into which the coil 30 rests. Above this second rotatable housing is a cover 24 on top of which sits a decorative front panel 16 and both the front panel knob housing 24 and the decorative front panel 16 can contain apertures 54 for the release of scent therefrom when the rotatable housing 22 is rotated.

In the center atop both the panel knob housing 24 and the decorative front panel 16 is a circular opening 26 for the placement therein of the actuation mechanism 28. The actuation mechanism 28 sits atop the spring 30 that provides a means for the actuation mechanism 28 to stay in the open position one activated and to push against to store energy when in the closed position.

The actuation mechanism 28 is quasi-cylindrical in shape and includes a top portion 32, a cylindrical wall 34 into which a cavity 36 is bored that is shaped to receive a scent cartridge 38. The cartridge 38 seen in detail in FIGS. 4-5 has a removable top surface 42 and a bottom surface 46 and a cylindrical wall 80 connecting the top surface 42 and bottom surface 46 when connected. The top surface contains a plurality of apertures 40, 50 having a variety of shapes as desired. These apertures 40, 50 allow the dry scent cartridges 44 housed therein to emit scent once the scent cartridges have been exposed to the immediately area through the actuation mechanism 28.

Figure 7:
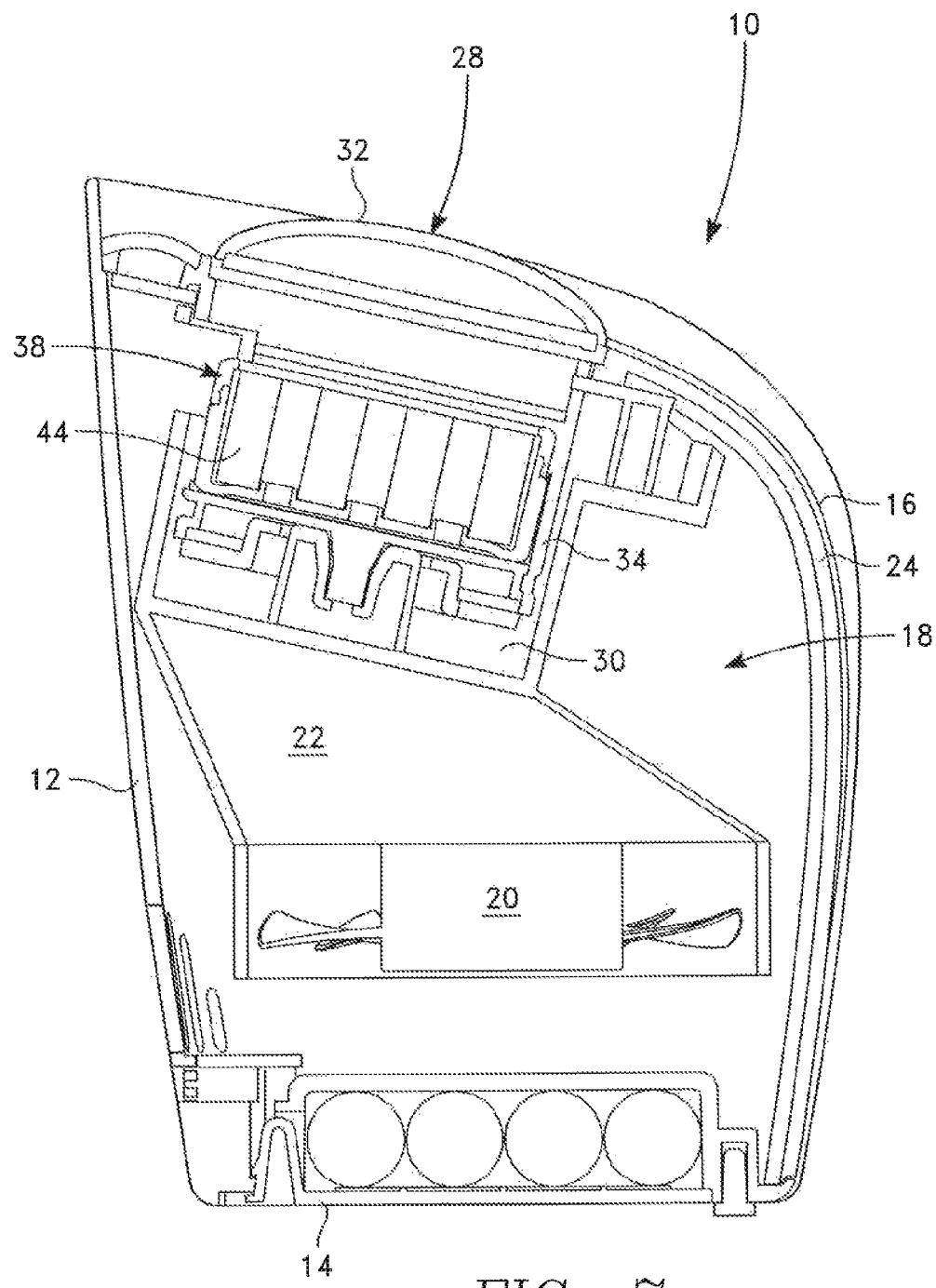
FIG. 7 is a cross-section side view of the stand alone unit of the scent diffuser of the instant invention

In the stand-alone device 10, a cartridge 38 is placed inside of the cavity 36 and the actuation device 28 is pushed downward to keep the diffuser 10 in the closed position when not in use (See FIGS. 3 and 7). When it is desired to be used, the actuation device 28 is depressed and through the energy stored in the spring 30, the actuation device 38 is raised into the open position (See FIGS. 1 and 2) thereby exposing the cavity 36 and the cartridge 38 housed therein to the air in the immediate area. Electrical power is supplied and the fan 20 propels the scent into the immediate area at the desired speed.

The actuation device 28 includes a rotatable knob 52 that allows for the adjustment of the speed of the diffusion once opened. Further apertures 54 can be placed on the top 32 of the device 10 through a disc 56 to allow for the emanation of the scent based on the desired speed.

Another embodiment 60 of the use of the dry porous pad with infused fragrance diffusion is illustrated in FIGS. 8-9 wherein a plug-in into an electrical socket is used to actuate the diffusion of scent. The dry porous pad 44 is housed in the cartridge 38 that includes the same top surface 42 with apertures 40, 50 on an adjacent disc as in the stand alone embodiment. A similar adjacent disc 64 covers the bottom of the porous pad 44. A decorative lid 66 may also be added to the top of the top disc 42.

The porous pad 44 in the cartridge 38 can then be placed in an interior space 68 of a second outer housing 70 which is proximate a fan 72 that sits on a plate 82 that mechanically connects through various slots and holes 84, 86 on a base 90 to a plug-in mechanism 74 wherein when the device is plugged in, the power supplied serves to activate the fan 72 and thereby disperse scent into the immediate environment.

A second embodiment of the plug-in is shown in FIG. 9 but in this embodiment, no fan is included and just heat is applied through the electricity to disperse the scent into the immediate environment.

The discussion included in this patent is intended to serve as a basic description. The reader should be aware that the specific discussion may not explicitly describe all embodiments possible and alternatives that are implicit. Also, this discussion may not fully explain the generic nature of the invention and may not explicitly show how each feature or element can actually be representative or equivalent elements. Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation, be it a variation of any apparatus embodiment, a method embodiment, or even merely a variation of any element of these. Particularly, it should be understood that as the disclosure relates to elements of the invention, the words for each element may be expressed by equivalent apparatus terms even if even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

What is claimed is:

1. A scent diffusing device comprising:
   a porous substrate infused with concentrated fragrance oil wherein said concentrated fragrance oil can be passively dispersed through the immediate environment or actively dispersed through the actuation of a mechanism to excite the scent molecules in said concentrated fragrance oil wherein said actuation is achieved through the application of heat.

2. The scent diffusing device as defined in claim 1 wherein said application of heat is achieved through the plugging into an electrical socket.

* * * * *